United States Patent [19]

Neustadt

[11] 4,159,335

[45] Jun. 26, 1979

[54] SUBSTITUTED ANILINO-2-THIAZOLINES

[75] Inventor: Bernard R. Neustadt, West Orange, N.J.

[73] Assignee: Schering Corporation, Kenilworth, N.J.

[21] Appl. No.: 872,130

[22] Filed: Jan. 25, 1978

Related U.S. Application Data

[60] Division of Ser. No. 668,385, Mar. 19, 1976, Pat. No. 4,081,547, which is a continuation-in-part of Ser. No. 528,603, Dec. 2, 1974, abandoned.

[30] Foreign Application Priority Data

Nov. 1, 1975 [CH] Switzerland ............... 15164/75

[51] Int. Cl.$^2$ .................................. C07D 277/04

[52] U.S. Cl. ..................... 424/270; 260/306.7 T

[58] Field of Search ............... 260/306.7 T; 424/270

[56] References Cited

U.S. PATENT DOCUMENTS

| | | | |
|---|---|---|---|
| 3,816,444 | 6/1974 | Narayanan et al. | 260/306.7 T |
| 4,081,547 | 3/1978 | Neustadt | 424/270 |

*Primary Examiner*—Nicholas S. Rizzo
*Attorney, Agent, or Firm*—Barbara L. Cowley Renda; Bruce M. Eisen

[57] ABSTRACT

Novel para-polyfluoroisopropyl-anilino-2-oxazolines and thiazolines are provided which exhibit potent antihypertensive properties without significant CNS depression.

14 Claims, No Drawings

SUBSTITUTED ANILINO-2-THIAZOLINES

This is a division of application Ser. No. 668,385, filed Mar. 19, 1976, now U.S. Pat. No. 4,081,547 which, in turn, is a continuation-in-part of my copending application Ser. No. 528,603, filed Dec. 2, 1974, which is hereby incorporated by reference now abandoned.

This invention relates to novel para-polyfluoroisopropyl-anilino-2-oxazolines and the corresponding 2-thiazolines which are useful in the treatment of mammalian hypertension. Used as such, they exhibit high potency with little or no depression of the central nervous system.

These compounds may be represented by the structural formula:

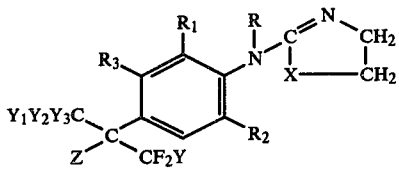

wherein
X is an oxygen or sulfur atom,
R is alkyl having 1 to 4 carbon atoms,
$R_1$, $R_2$ and $R_3$ are independently hydrogen, bromine, chlorine, fluorine, lower alkyl, lower alkoxy, lower alkanoyloxy or nitro,
Y, $Y_1$, $Y_2$ and $Y_3$ are independently hydrogen, chlorine or fluorine,
Z is independently hydrogen, hydroxy, lower alkoxy, lower alkanoyloxy, chlorine or fluorine.

The term "lower" as used in the above definitions means that the alkyl portion of the subject group contain 1 to 6 carbon atoms. In the case of "lower alkanoyloxy" this portion contains 2 to 6 carbon atoms.

Within the broad scope of Formula I there are, of course, certain preferential embodiments. $R_3$ is preferably hydrogen. $R_1$ and $R_2$ are preferentially hydrogen or lower alkyl. $R_1$ and $R_2$ each being a lower alkyl group is a preferred embodiment. Z is preferably a hydroxy group.

X is preferably an oxygen atom, i.e. an oxazoline. A highly preferred compound is 2-[4-(hexafluoro-2-hydroxy-2-propyl)-N-methylanilino]-2-oxazoline.
Other preferred oxazolines within the scope of this invention include:

2-[4-(tetrafluoro-1,3-dichloro-2-hydroxy-2-propyl)-N-methylanilino]-2-oxazoline
2-[4-(hexafluoro-2-methoxy-2-propyl)-N-methylanilino]-2-oxazoline
2-[N,2,6-trimethyl-4-(hexafluoro-2-hydroxy-2-propyl)anilino]-2-oxazoline
2-[4-(hexafluoro-2-hydroxy-2-propyl)-2-chloro-N-methylanilino]-2-oxazoline
2-[4-(hexafluoro-2-hydroxy-2-propyl)-N,2-dimethylanilino]-2-oxazoline
2-[4-(hexafluoro-2-hydroxy-2propyl)-N-n-propylanilino]-2-oxazoline
2-[2,6-diisopropyl-4-(hexafluoro-2-hydroxy-2-propyl)-N-methylanilino]-2-oxazoline
2-[4-(1,1,1-trifluoro-2-hydroxy-2-propyl)-N-methylanilino]-2-oxazoline
2-[4-(3-chloropentafluoro-2-hydroxy-2-propyl)-N-methylanilino]-2-oxazoline
2-[4-(2-acetoxyhexafluoro-2-propyl)-N-methylanilino]-2-oxazoline
2-[4-(2-chlorohexafluoro-2-propyl)-N-methylanilino]-2-oxazoline
2-[2,6-dichloro-4-(hexafluoro-2-hydroxy-2-propyl)-N-methylanilino]-2-oxazoline
2-[2,6-diethyl-4-(hexafluoro-2-hydroxy -2-propyl)-N-methylanilino]-2-oxazoline
2-[2-chloro-4-(hexafluoro-2-hydroxy-2propyl)-N,6-dimethylanilino]-2-oxazoline
2-[4-(hexafluoro-2-hydroxy-2propyl)-2-methoxy-N-methylanilino]-2-oxazoline
2-[2-fluoro-4-(hexafluoro-2-hydroxy-2-propyl)-N-methylanilino]-2-oxazoline
2-[4-(hexafluoro-2-hydroxy-2-propyl)-2,5-dimethyl-N-methylanilino]-2-oxazoline
2-[4-(hexafluoro-2-hydroxy-2-propyl)-2,6-dimethoxy-N-methylanilino]-2-oxazoline
2-[N-ethyl-4-(hexafluoro-2-hydroxy-2-propyl)anilino]-2oxazoline
2-[4-(hexafluoro-2-propyl)-N-methylanilino]-2-oxazoline A preferred thiazoline is 2-[4-(hexafluoro-2-hydroxy-2-propyl)-N-methylanilino]-2-thiazoline. Other thiazolines within the scope of this invention includes:

2-[4-hexafluoro-2-hydroxy-2-propyl)-N-ethylanilino]-2-thiazoline
2-[N,2,6-trimethyl-4-(hexafluoro-2-hydroxy-2-propyl)anilino]-2-thiazoline
2-[4-(tetrafluoro-1,3-dichloro-2-hydroxy-2-propyl)-N-methylanilino]-2-thiazoline.

Similarly, the other oxazolines listed above have corresponding thiazolines within the scope of this invention.

The above oxazolines and thiazolines of Formula I may be administered per se or in the form of their pharmaceutically acceptable acid addition salts. Exemplary of the latter are those formed with maleic, acetic, phthalic, succinic, lactic, tartaric, citric, malic, cinnamic, methane-sulphonic, hydrochloric, hydrobromic, sulfuric and phosphoric acids. The salts may be prepared by the standard technique of precipitation by treatment of a solution of the free base in a suitable organic solvent with the desired acid. Further purification, if desired, may be effected by recrystallization.

The art, in retrospect, discloses that other substituted anilino-2-oxazolines have hypotensive activity, e.g. U.S. Pat. Nos. 3,453,284; 3,499,083 and 3,499,084 and Belgian Pat. Nos. 704,392; 704,393 and 704,396. However, in these prior art oxazolines the aniline nitrogen atom is unsubstituted and the critical para-polyfluoroisopropyl phenyl substituent is not suggested. Moreover, these compounds are taught to be central nervous system depressants.

Similarly, the art discloses that polyfluoroisopropyl-substituted anilines are known and in some cases reported to have hypotensive activity, e.g. U.S. Pat. Nos. 3,405,177; 3,541,152; 3,594,418; 3,772,273 and Gilbert, J. Org. Chem., Vol. 30 (1965) 1001. The compounds of my invention exhibit much more potent and useful hypotensive activity than do the foregoing anilines. Those compounds of Formula I wherein X is oxygen can be prepared by the intramolecular condensation of a urea of Formula II:

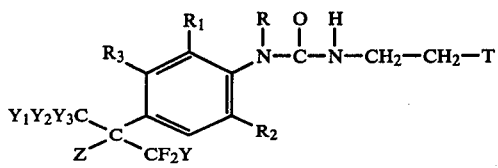

wherein R, R$_1$, R$_2$, R$_3$, Y, Y$_1$, Y$_2$, Y$_3$ and Z are as above defined and T is a labile leaving group such as halogen, or a sulfonic acid ester moiety; e.g. tosyl and mesyl. Chlorine is the preferred T group. The condensation can be effected by heating the urea in an aqueous alcoholic vehicle, preferably under acidic conditions. The urea of Formula II can in turn be prepared by methods described in my copending patent application Ser. No. 528,603; and other methods described in the literature such as the above-cited patents.

Those compounds of Formula I wherein X is sulfur can be directly prepared by the condensation of chloro- or bromo- ethylisothiocyanate with the corresponding aniline of Formula III:

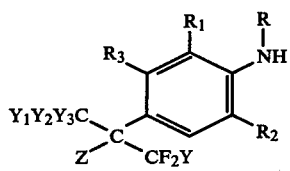

wherein R, R$_1$, R$_2$, R$_3$, Y, Y$_1$, Y$_2$ and Z are as above defined. The two reactants are refluxed in an inert solvent, e.g. benzene, and the corresponding thiazoline hydrohalide is removed and purified in the conventional manner.

The following examples illustrate the preparation of representative compounds of my invention.

EXAMPLE 1

2-[4-(hexafluoro-2-hydroxy-2-propyl)-N-methylanilino]-2-oxazoline

Dissolve 10.0 g (26 m.mole) of N-(2-chloroethyl)-N'-[4-(hexafluoro-2-hydroxy-2-propyl)phenyl]-N'-methylurea in a mixture of 50 ml of methanol and 100 ml of water. Heat for one hour on a steam bath. Concentrate, and partition between 1N aqueous sodium bicarbonate solution and ether (diethyl) and then extract with 200 ml of 1N hydrochloric acid. Add sodium bicarbonate and then extract with 200 ml of ether. Dry the ether extract and concentrate to obtain 7.8 g of the title compound as a white solid, m.p. 188°–190° C. The salts may be prepared by standard techniques such as by treatment of a solution of the free base in a suitable organic solvent, e.g. ether, with the desired acid, e.g. hydrochloric, and then filtering off the precipitated salt. The hydrochloride salt melts at 147°–149° C.

EXAMPLE 2

2-[4-(hexafluoro-2-hydroxy-2-propyl)-N-methylanilino]-2-thiazoline

Combine 11.0 g p-(hexafluoro-2-hydroxy-2-propyl)-N-methylaniline (0.04 mole) and 9.7 g 2-chloroethylisothiocyanate (0.08 mole) in 100 ml benzene. Heat to reflux 3 hours and filter off solid. Dissolve in 300 ml water, basify with sodium carbonate. Extract with ether then dry and concentrate. Recrystallize residue from hexane-ether to give crystals, m.p. 160°–3° C. The fumarate salt, prepared in methanol, has m.p. 175°–7° C.

EXAMPLE 3

2-[4-(hexafluoro-2H-2-propyl)-N-methylanilino]-2-oxazoline

To a solution of 1.6 g 2-[4-(2-chlorohexafluoro-2-propyl)-N-methylanilino]-2-oxazoline bisulfate (0.003 mole) in 40 ml ethanol add 0.1 g 5% palladium on charcoal. Shake 3 hours with hydrogen at 3 atm. pressure, filter and concentrate. Partition between ethyl acetate and aqueous sodium bicarbonate. Dry and concentrate the ethyl acetate. Treat the residual oil with 0.2 g orthophosphoric acid in methanol, dilute with ether and filter to give the phosphate salt, m.p. 93°–7° C.

EXAMPLE 4

2-[4-(2-chlorohexafluoro-2-propyl)-N-methylanilino]-2-oxazoline

Add 5.5 g of a 57% solution of sodium hydride in mineral oil (0.13 mole) to a solution of 22.7 g N-(2-chloroethyl)-N'-[4-(hexafluoro-2-hydroxy-2-propyl)-phenyl]-N'-methylurea (0.06 mole) in 100 ml 1,2-dimethoxyethane. Stir one hour and then add slowly 15.1 g thionyl chloride (0.13 mole). After one hour, pour onto 800 ml water. Filter off the solid, dissolve in 200 ml methanol, and decant from the mineral oil. To the methanol add 16 g sodium borohydride (0.4 mole). Concentrate and dissolve the residue in ether. Wash with water and concentrate to give a cream solid. Dissolve the solid in 40 ml 2N sulfuric acid and 40 ml methanol. Reflux 1 hour and concentrate partially. Partition between ethyl acetate and aqueous sodium bicarbonate. Dry and concentrate the ethyl acetate. Treat the residual oil in ether with ethereal sulfuric acid and filter off the solid. Partition between ethyl acetate and aqueous sodium bicarbonate. Dry the ethyl acetate, concentrate and distill, b.p. 123°–31° (0.1mm). Treat the distillate in ether with ethereal sulfuric acid to give the bisulfate salt, m.p. 143°–6° C.

EXAMPLE 5

2-[4-(hexafluoro-2-methoxy-2-propyl)-N-methylanilino]-2-oxazoline

Add 8.3 g K$_2$CO$_3$ (0.06 mole) to a solution of 11.3 g N-(2-chloroethyl)-N'-[4-(hexafluoro-2-hydroxy-2-propyl) phenyl]-N'-methylurea (0.03 mole) and 17.0 g (0.12 mole) of methyl iodide in 120 ml acetonitrile. Stir 4 days, filter, and concentrate the filtrate. Dissolve the residue in ether and wash with water. Dry and concentrate the ether. Boil the residue 1 hour in 100 ml 50% methanol. Concentrate and partition between ether and 1N hydrochloric acid. Neutralize the aqueous layer with sodium bicarbonate, extract with ether, dry and concentrate the ether. Dissolve the oil in 10 ml methanol and treat with 2.0 g fumaric acid. Pour the solution into ether and filter to give the fumarate salt, m.p. 89°–91° C.

EXAMPLE 6

2-[4-(2-acetoxyhexafluoro-2-propyl)-N-methylanilino]-2-oxazoline

Add 2.2 g 57% sodium hydride (0.05 mole) to a solution of 17.1 g 2-[4-(hexafluoro-2-hydroxy-2-propyl)-N-methylanilino-]-2-oxazoline in 150 ml 1,2-dimethoxyethane. After 1 hour, add 3.9 g acetyl chloride (0.05 mole). After 1 hour additional, filter and concentrate. Dissolve the residue in ether and 1N hydrochloric acid. Neutralize the aqueous layer with sodium bicarbonate. Extract with ether and dry over magnesium sulfate. Treat the solution with etheral hydrochloric acid. Collect the solid and recrystallize from methanol ether to give the hydrochloride salt, m.p. 102°–4° C.

A number of agents are known in the treatment of hypertension. Certain of these, for example reserpine, are effective in lowering the blood pressure in some patients but in other patients give rise to undesirable and well known side effects.

The compounds of the present invention have been found to exhibit useful and potent anti-hypertensive activity. They produce rapid onset of such activity. Further, representative compounds of the invention have been found to be particularly active as anti-hypertensive agents while avoiding or mitigating some of the deleterious side effects, such as central nervous system depression associated with known anti-hypertensive agents. Based on laboratory tests, it is considered that the effective dosage (the $ED_{50}$) by oral administration for a compound of the present invention will typically lie within the range of from 0.01 to 2 mg/kg of mammalian weight per day. For the preferred compound, 2-[4-hexafluoro-2-hydroxy-2-propyl)-N-methylanilino]-2-oxazoline, the contemplated daily human dose is about 0.6 to 10 mg.

The required daily dosage may be administered in single or divided doses. The exact dose to be administered will, of course, be dependent upon where the compound in question lies within the above quoted dosage ranges and upon the age and weight of the subject mammal.

The compounds are administered orally. In any event, a suitable pharmaceutical carrier is employed, with the carrier selected according to the physical properties of the compound in the pharmaceutical composition. The carrier should not react chemically with the compound to be administered. The preparations containing the active ingredients may typically be in the form of tablets, capsules, syrups, elixirs or suspensions.

Representative formulations for the compounds of the general formula I will now be illustrated by way of the following Examples.

Tablet Formulations

| Formulation I | Milligrams per Tablet |
|---|---|
| 2-[4-(hexafluoro-2-hydroxy-2-propyl)-N-methylanilino]-2-oxazoline | 1 |
| Lactose, direct compression grade | 222 |
| Microcrystalline cellulose | 30 |
| Sodium Lauryl Sulfate | 20 |
| Corn starch | 25 |
| Magnesium stearate | 2 |
| | 300 |

Mix together the stated active ingredient, lactose, microcrystalline cellulose, sodium lauryl sulfate and corn starch. Pass through a No. 40 screen. Add the magnesium stearate, mix and compress into desired shape on a tablet machine.

| Formulation II | Milligrams per Tablet |
|---|---|
| 2-[4-(hexafluoro-2-hydroxy-2-propyl)-N-methylanilino]-2-oxazoline | 1 |
| Lactose, U.S.P. | 240 |
| Dicalcium phosphate | 57 |
| Sodium Lauryl Sulfate | 20 |
| Polyvinylpyrrolidine | 10 |
| Water 50 ml/1000 tablets | |
| Corn Starch | 20 |
| Magnesium Stearate | 2 |
| | 350 |

Mix together the stated active ingredient, lactose, dicalcium phosphate and sodium lauryl sulfate. Screen the above mixture through a No. 60 screen and granulate with an aqueous solution containing polyvinylpyrrolidone. Add additional water, if necessary, to bring the powders to a pasty mass. Add corn starch and continue mixing until uniform granules are formed. Pass through a No. 10 screen, tray and dry in an oven at 40° C. for 12 to 14 hours. Reduce the dried granulation through a No. 16 screen. Add magnesium stearate, mix and compress into desired shape on a tablet machine.

Capsule Formulations

| Formulation I | Milligrams per Capsule |
|---|---|
| 2-[4-(hexafluoro-2-hydroxy-2-propyl)-N-methylanilino]-2-oxazoline | 1 |
| Lactose, U.S.P. | 222 |
| Microcrystalline Cellulose | 30 |
| Sodium Lauryl Sulfate | 20 |
| Corn Starch | 25 |
| Magnesium Stearate | 2 |
| | 300 |

Procedure

Mix together the stated active ingredient, lactose, microcrystalline cellulose, sodium lauryl sulfate and corn starch. Pass through a No. 80 screen. Add the magnesium stearate, mix and encapsulate into the proper size two-piece gelatin capsule.

In treating certain patients with the compounds of this invention it may be desirable to include other pharmaceutically active ingredients in the same dosage unit. For example, in treating patients in whom salt and water retention is a problem, effective amounts of conventional diuretics can be incorporated, such as the thiazide diuretics, e.g. hydrochlorothiazide or trichloromethiazide. Similarly, in treating patients in whom tachycardia might be a problem, an effective amount of a pharmaceutically acceptable beta-blocking agent can be included, e.g. propnanolol. The dosage unit could even contain a combination of a compound of this invention, e.g. 2-[4-(hexafluoro-2-hydroxy-2-propyl)-N-methylanilino]-2-oxazoline, a diuretic, e.g. hydrochlorothiazide and a beta-blocker, e.g. propnanolol.

Numerous other variants of the above compounds, compositions and methods will be apparent to one skilled in the art within the scope of this invention.

I claim:

1. A compound of the formula

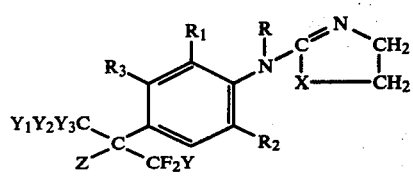

wherein

X is a sulfur atom,

R is alkyl having 1 to 4 carbon atoms, $R_1$, $R_2$ and $R_3$ are independently hydrogen, bromine, chlorine, fluorine, lower alkyl, lower alkoxy, lower alkanoyloxy or nitro, Y, $Y_1$, $Y_2$ and $Y_3$ are independently hydrogen, chlorine or fluorine, Z is independently hydrogen, hydroxy, lower alkoxy, lower alkanoyloxy, chlorine or fluorine, and the pharmaceutically acceptable salts thereof.

2. A compound according to claim 1 wherein R is methyl.

3. A compound according to claim 1 wherein $R_1$, $R_2$ and $R_3$ are each hydrogen.

4. A compound according to claim 1 wherein Z is hydroxy.

5. A compound according to claim 1 wherein $R_3$ is hydrogen.

6. A compound according to claim 5 wherein $R_1$ and $R_2$ are each lower alkyl.

7. A compound according to claim 1 wherein Y, $Y_1$, $Y_2$ and $Y_3$ are each fluorine.

8. A compound according to claim 7 wherein Z is hydroxy.

9. A compound according to claim 1 wherein X is sulfur.

10. A compound according to claim 9 wherein Z is hydroxy.

11. A compound according to claim 10, said compound being 2-[4-(hexafluoro-2-hydroxy-2-propyl)-N-methylanilino]-2-thiazoline.

12. A pharmaceutical composition adopted to treat hypertension comprising an oral dosage of an antihypertensively effective amount of a compound of claim 1 in a pharmaceutically acceptable diluent.

13. A composition according to claim 12 in the form of a solid oral dosage unit.

14. A method of treating hypertension comprising orally administering to a hypertensive mammal a composition of claim 12.